United States Patent
Ootatsume et al.

(10) Patent No.: US 6,723,287 B1
(45) Date of Patent: Apr. 20, 2004

(54) MEASURING SYSTEM FOR AUTOMATIC CHEMICAL ANALYZER

(75) Inventors: Yoshio Ootatsume, Yamanashi (JP); Kiyoshi Kawashima, Tokyo (JP); Minoru Inatsugu, Saitama (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 09/523,113

(22) Filed: Mar. 10, 2000

(30) Foreign Application Priority Data

Mar. 10, 1999 (JP) .......................................... 11-063537

(51) Int. Cl.[7] .......................... B32B 27/04; G01N 21/00
(52) U.S. Cl. .......................... 422/64; 422/63; 422/65; 422/67; 422/68.1; 422/82.05; 422/82.09; 436/43; 436/45; 436/47; 436/164; 436/165; 436/171; 198/465.2; 356/246; 356/213; 318/685; 318/698
(58) Field of Search ................. 422/63–65, 67, 422/68.1, 82.05, 82.09; 436/43, 45, 47, 164–165, 171; 198/465.2; 356/246, 213; 318/698, 685

(56) References Cited

U.S. PATENT DOCUMENTS

| | | | | | |
|---|---|---|---|---|---|
| 3,740,760 A | * | 6/1973 | Johnson et al. | ........... | 346/74 E |
| 3,878,378 A | * | 4/1975 | Johnson et al. | ......... | 235/151.35 |
| 4,043,756 A | * | 8/1977 | Sommervold | ............. | 23/260 R |
| 4,101,383 A | * | 7/1978 | Wyatt et al. | .......... | 195/103.5 R |
| 4,308,231 A | * | 12/1981 | Kolber et al. | .................. | 422/64 |
| 4,329,061 A | * | 5/1982 | Snook et al. | ................ | 356/414 |
| 4,549,809 A | * | 10/1985 | Minekane et al. | .......... | 356/436 |
| 4,798,703 A | * | 1/1989 | Minekane | .................... | 422/65 |
| 5,478,750 A | * | 12/1995 | Bernstein et al. | ........... | 436/164 |
| 6,031,316 A | * | 2/2000 | Kataoka | ..................... | 310/316 |

FOREIGN PATENT DOCUMENTS

JP            6258327          9/1994

* cited by examiner

Primary Examiner—Jill Warden
Assistant Examiner—LaToya Cross
(74) Attorney, Agent, or Firm—Webb Ziesenheim Logsdon Orkin & Hanson, P.C.

(57) ABSTRACT

There is disclosed a measuring system that is for use with an automatic chemical analyzer and accomplishes accurate measurement reproducibility and low cost. The system has a turntable on which plural reaction cells are arranged circumferentially. A light source and a spectroscopic detector are located on opposite sides of the reaction cell in a detection position. The amount of light transmitted through the cell is measured. A motor having an encoder is connected to the turntable. The output signal from the detector corresponding to each reaction cell is accepted in response to the output signal from the encoder.

8 Claims, 3 Drawing Sheets

MEASURING SYSTEM FOR AUTOMATIC CHEMICAL ANALYZER

BACKGROUND OF THE INVENTION

1. Field of the Invention

The present invention relates to a measurement system for an automatic chemical analyzer.

2. Description of the Related Art

A measurement system is known which is used with an automatic chemical analyzer and which comprises a turntable on which reaction cells are arranged circumferentially and a detector located at a given position relative to the turntable. As the turntable rotates, the detector measures the absorbances of the reaction cells in turn. In this measurement system, as the turntable turns, the reaction cells pass across the front surface of the detector in turn. The output signal from the detector must be sampled just when each reaction cell arrives at the detection position, whereby the absorbance of each cell is measured.

If the timing of the sampling were not accurately adjusted, the absorbance of a portion different from a liquid sample would not be measured. As a result, the measured value would involve error. Therefore, the setting of the sampling timing is quite important. In a known system, a slit, a chopper, a shutter, and other components are mounted at positions corresponding to reaction cells on the turntable to sense the arrival of each reaction cell at the detection position by an optical sensor.

With the above-described method using an optical sensor, if the number of reaction cells placed on the turntable increases, and if the speed of operation becomes higher, then the slit, chopper, shutter, and other components must be accurately aligned to the positions of the reaction cells on the turntable. As the number increases, the size of each reaction cell decreases. This makes it more difficult to make the alignment, which in turn will deteriorate the cost effectiveness.

SUMMARY OF THE INVENTION

It is an object of the present invention to provide a measurement system which is used with an automatic chemical analyzer and permits accurate measurement reproducibility and low-cost measurements.

In accordance with the teachings of the present invention, a measurement system is provided for use with an automatic chemical analyzer having a turntable on which reaction cells, each holding a liquid sample aliquot, are arranged circumferentially and a detector placed in a given position relative to the turntable and acting to measure the absorbances of the reaction cells in turn as the turntable rotates. The measurement system comprises an encoder connected with the turntable, a counter for creating an address signal from the output signal from the encoder as the turntable rotates, and a comparator for comparing the address signal with address values previously found when the reaction cells arrived at a detection position. The address signal is obtained as the count value from the counter. The comparator produces a coincidence signal when a match is found. In response to the coincidence signal, the output signal from the detector corresponding to each reaction cell is started to be accepted.

In one embodiment of the present invention, the aforementioned measurement system has a register and a readout circuit. The register holds address values obtained when the reaction cells reach the detection position. The readout circuit sequentially reads address values for each reaction cell to be measured next from the register in response to the coincidence signal described above and sends the address values to the comparator described above.

An address value obtained when each reaction cell reaches the detection position can be determined based on data obtained by sampling the output signal from the detector in synchronism with the encoder output signal over the whole circumference of the turntable while the reaction cells hold no liquid solution or a liquid exhibiting no absorbance in the measured spectral range is put in the cells.

Furthermore, the address value obtained when each reaction cell reaches the detection position can be determined based on data obtained by sampling the output signal from the detector in synchronism with the encoder output signal over the whole circumference of the turntable while aliquots of a liquid exhibiting absorbance in the measured spectral range are put in the cells.

Other objects and features of the present invention will appear in the course of the description thereof, which follows.

DESCRIPTION OF THE PREFERRED EMBODIMENTS

The preferred embodiments of the present invention are hereinafter described.

Figure 1A:
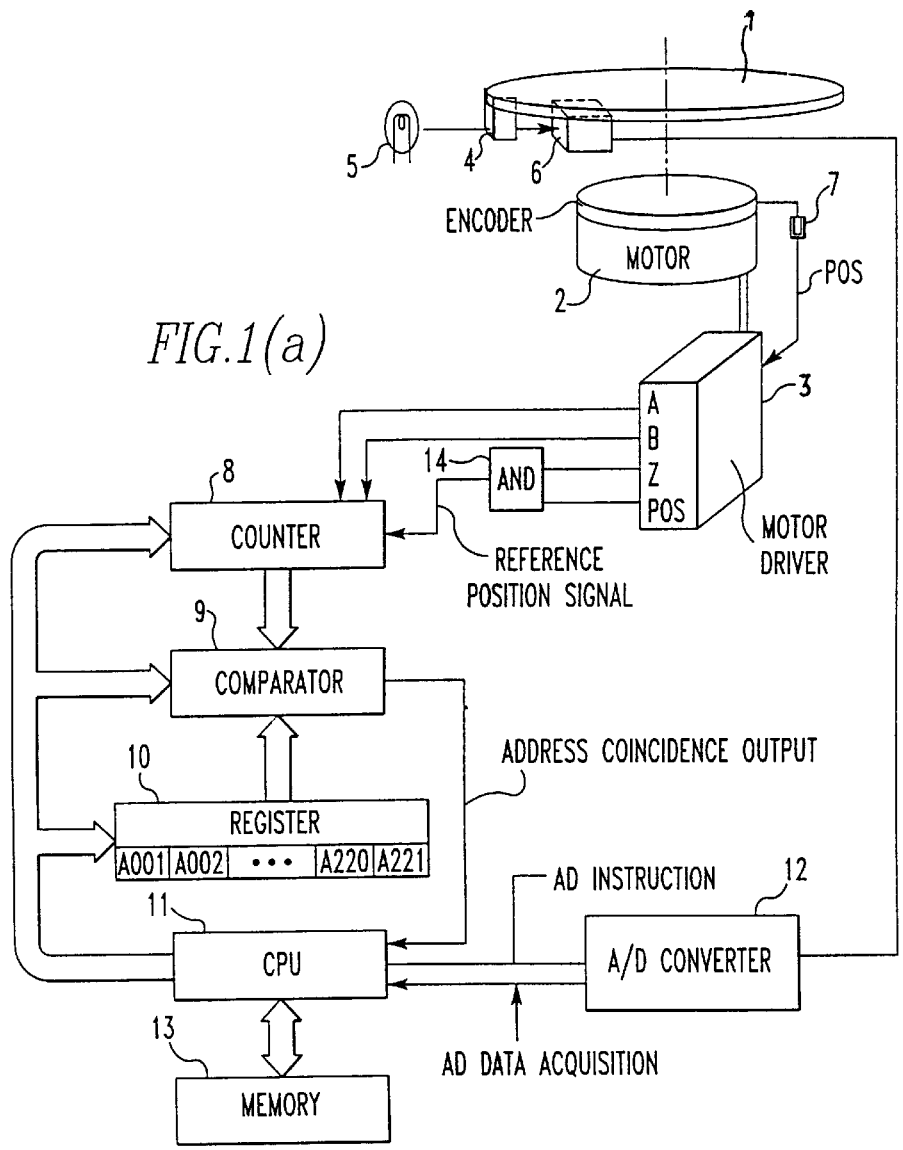
FIG. 1(a) is a block diagram partially in perspective view of a measuring system for use with an automatic chemical analyzer in accordance with the present invention.

FIG. 1(a) illustrates a measurement system for use with an automatic chemical analyzer, the measurement system being built in accordance with the present invention. The measurement system has a turntable 1 on which plural (e.g., 221) reaction cells 4 are circumferentially equally spaced from each other. Note that only one of the cells 4 is shown in FIG. 1(a). Each reaction cell 4 holds an aliquot of liquid sample to be measured. A light source 5 and a spectroscopic detector 6 are mounted under the turntable 1 such that the light source 5 and the detector 6 are located on opposite sides of the reaction cell 4 in a detection position. The amount of light transmitted through the reaction cell 4 in the detection position is measured by the spectroscopic detector 6. The turntable 1 is driven by a direct drive motor 2. A position sensor 7 is mounted at a given position on the circumference of either the turntable 1 or the motor 2. This position sensor 7 produces a single pulse whenever a given portion of the turntable arrives at a reference position, i.e., produces one pulse per revolution.

The direct drive motor 2 generates a pulse whenever the motor itself rotates through a given step angle. In particular, an encoder capable of position detection is mounted to the driving shaft of the motor 2. A direct drive motor driver 3 controls the direction and angular position of the motor according to the output signal from the encoder.

The encoder used in this embodiment is a two-phase encoder producing signals of phases A and B that are shifted in phase by 90°. This encoder produces 122,880 pulses (or two times, four times, or one-half) of phases A and B per revolution and generates a Z-phase signal consisting of 120 pulses per revolution. This Z-phase signal is used by an AND circuit 14 that ANDs the Z-phase signal and the output signal from the position sensor to create a reference position signal. The signal of phase A leads or lags the signal of phase B, depending on the direction of rotation of the motor.

An encoder counter 8 is an up-down counter for counting the pulses of the signal of phase A or B. The counter 8 counts forward or backward, depending on whether the signal of phase A leads or lags, respectively, the signal of phase B. Where the turntable rotates only in one direction, only the pulses of the signal of phase A or B can be counted to monitor the angular position of the turntable.

Figure 1B:
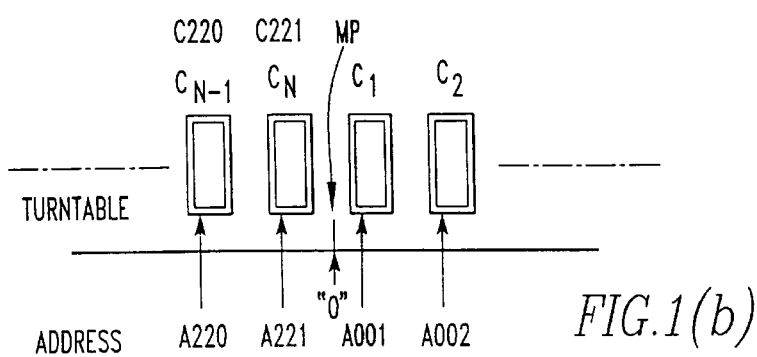
FIG. 1(b) is a schematic diagram illustrating turntable positions relative to the midpoint reference position (MP)

The positions of the reaction cells arranged circumferentially on the turntable 1 can be addressed at the resolution (i.e., the number of pulses per revolution) of the encoder. In the present embodiment, 221 (N=221) reaction cells C1–C221 are disposed on the turntable at uniform spacing as shown in FIG. 1(b). Therefore, the pitch between the reaction cells is 122880/221=556 pulses in terms of encoder pulses.

The midpoint MP between the reaction cells C221 and C1 on the turntable 1 is taken as a reference position for the turntable. The position at which the position sensor is mounted is so selected that an output pulse is produced when the reference position arrives at a detection position where detection is made by the detector. The total count of the encoder counter 8 is reset to 0 (i.e., cleared) in response to ANDing of the Z-phase signal from the direct drive motor driver 3 and the position sensor output signal, the ANDing being obtained by the AND circuit 14. The output signal from the AND circuit 14 indicating the ANDing is referred to as the reference position signal. When this reference position signal is produced, the reference position MP of the turntable is in the detection position. The total count of the counter 8 is cleared at this time and set to 0, which indicates the address of the reference position (i.e., the origin). If the output pulse from the position sensor has a sufficiently sharp rising edge, it is not necessary to AND the Z-phase signal and the position sensor signal; the encoder counter 8 can be cleared only by the position sensor signal.

The encoder counter 8 counts the encoder pulses during rotation of the turntable and increments. When one full rotation is made, the counter 8 is cleared by the reference position signal. Accordingly, the total count of the encoder count value varies from 0 to 122,879 and then is cleared by the reference position signal. When the reference position of the turntable arrives at the reference position during each revolution of the turntable, the position indicated by address 0 is taken as the reference position or the origin. Count values 0 to 122,879 of the encoder counter 8 are assigned to the positions taken along the circumference (360°) of the turntable, and thus these positions are addressed.

As shown in FIG. 1(a), a setting register 10 has been previously loaded with addresses A001–A221 of the measurement starting points determined for all the reaction cells C1–C221. At each starting point, the output signal from the detector 6 is sampled and started to be taken as a digital signal. The address of the measurement starting point for each reaction cell has been previously determined according to results of photometric measurements of the reaction cells along the whole circumference of the turntable as described later.

When the reaction cells are filled with a sample and measurements are made, a comparator 9 compares the total count of the encoder counter 8 (the present address value) with the address values of the measurement starting point for the reaction cells C1, C2, . . . , C221. The address values are sequentially read from the setting register 10 under instructions from a CPU 11. If a match is found, an address coincidence output is sent to the CPU 11. Then, the CPU 11 instructs an A/D converter 12 to accept data from the detector 6 (i.e., start of a measurement), and reads the address value for the next reaction cell from the setting register 10. The analog-to-digital conversion and acceptance of data by the A/D converter 12 are done in synchronism with the encoder pulses. Values about a predetermined number of sampling points from the measurement starting point are accumulated. In this way, data about absorbance is obtained from each reaction cell. In practice, reference accumulation data measured under totally dark conditions is subtracted from the accumulation value measured as described above. In some cases, the accumulation value assumes a negative value by the effect of noises. In these cases, the value is set to 0.

The detection resolution of the encoder can be varied and measurements are performed by multiplying the number of pulses of phase A or B of the encoder by an integer (e.g., 2 or 4) or by halving the number of pulses. Furthermore, light transmitted through reaction cells may be diffracted by a diffraction grating and detected by a photodiode array. The analog signal is converted into digital form for each wavelength. In this way, plural kinds of tests corresponding to the wavelengths can be performed.

Figure 2A:
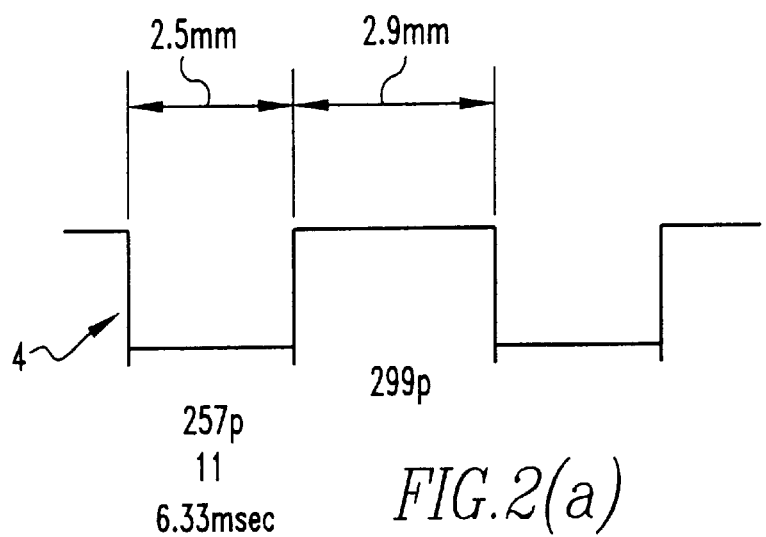
FIG. 2(a) is a diagram illustrating the relations among the width of reaction cells, the spacing between the reaction cells, the number of encoder pulses, and time intervals.
Figure 2B:
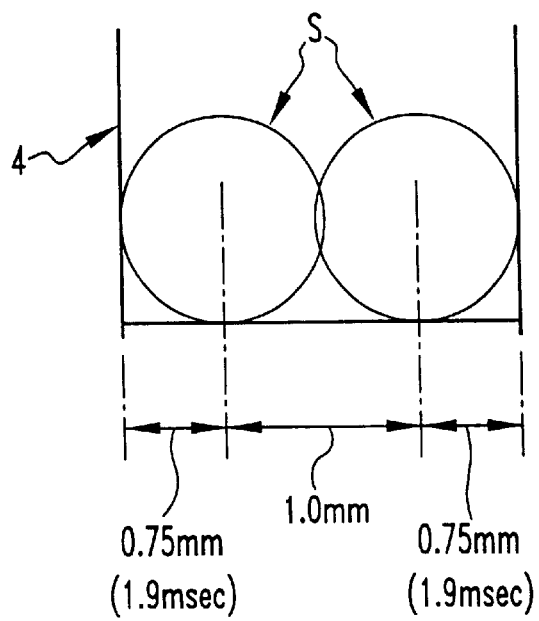
FIG. 2(b) is a diagram illustrating a measurement starting point and a measurable interval based on the width of a slit in a spectroscopic detector.

The manner in which the measurement starting address for each reaction cell is established is described below. FIGS. 2(a) and 2(b) illustrate the relations among the width of reaction cells, the spacing between them, the number of encoder pulses, and time intervals. FIG. 2(b) illustrates the measurement starting point and measurable intervals based on the width of a slit in a spectroscopic detector. In FIGS. 2(a) and 2(b), indicated by numeral 4 are the reaction cells, and indicated by S is the slit in the spectroscopic detector. The parameters used in this embodiment are as follows:

number of reaction cells: 221
width of reaction cells (inside dimension): 2.5 mm
pitch between reaction cells: 5.4 mm
slit diameter: 1.5 mm
resolution of encoder: 122,880 pulses per revolution
rotational speed of direct drive motor: 0.33 rps As illustrated in FIG. 2(a), expressing the width 2.5 mm of the reaction cells in terms of the number of encoder pulses (the number of points) results in (122,880/221)·2.5 mm/5.4 mm=257 points Converting the width 2.5 mm of the reaction cells into time gives rise to 257·1/(122,880·0.33)=6.33 msec Where it is assumed that the slit S moves relative to a reaction cell 4 as shown in FIG. 2(b), the time for which the slit S completely overlaps the reaction cell 4 is a measurable interval during which a sample can be measured correctly. In the present embodiment, the slit S is 1.0 mm. Taking this time interval as the measurable interval and expressing it in terms of the number of encoder pulses (the number of measurable points) gives (122,880/221)·1 mm/5.4 mm=102 points Converting this into time results in 2.5 msec. The distance from the edge of each reaction cell (outer wall) to a measurable point (inner wall) is (122,880/221)·0.75 mm/5.4 mm=77 points Converting this into time gives rise to 1.9 msec. In this way, the number of points from the reaction cell edge to the measurable point (measurement starting point) is determined. Also, the number of points of the measurable interval is determined.

As mentioned previously, if the edges of individual reaction cells are found from the results of measurements previously made of all the reaction cells over the whole circumference, an address at which a measurement is started is found for each reaction cell in the manner described below.

Figure 3:
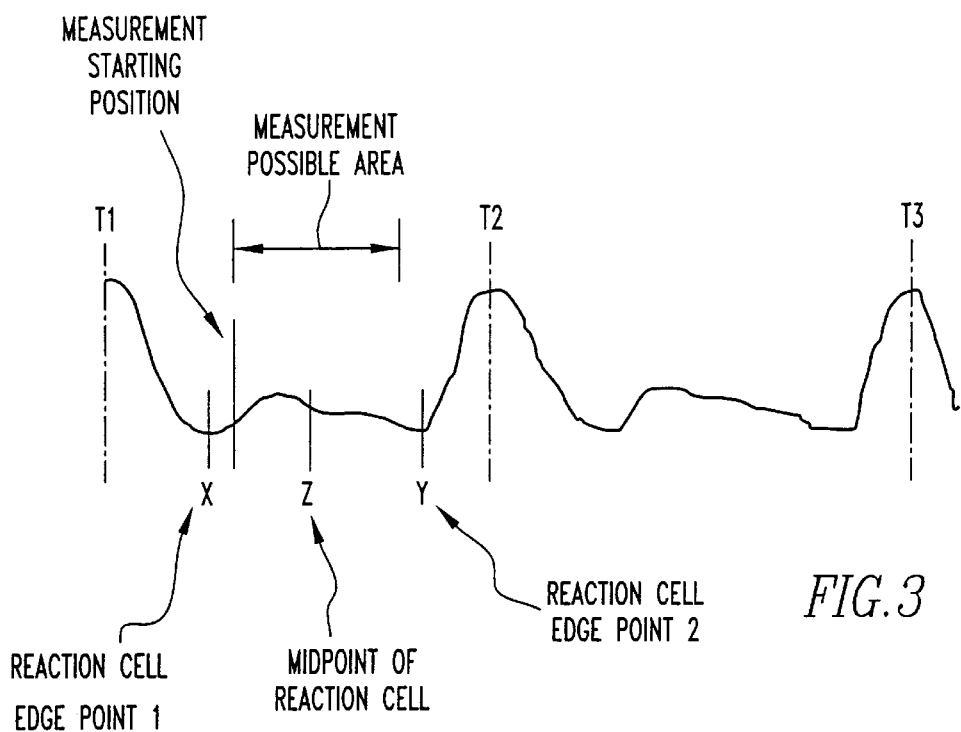
FIG. 3 is a diagram illustrating a method of finding a position at which measurement of a reaction cell is started.

FIG. 3 illustrates a method of finding the position at which a measurement of a reaction cell is started. In this example, prior to measurement of a sample, the reaction cell is measured while (1) no liquid solution is held in the cell, (2) a solution exhibiting no absorbance in the measured spectral range is held in the cell, or (3) pure water is held in the cell. In this figure, T1, T2, and T3 indicate equally spaced positions obtained by dividing the whole circumference of the turntable by the number of reaction cells. As described above, the pitch between the successive reaction cells corresponds to 556 pulses. The amount of light is measured over the whole circumference (i.e., at 122,880 points) by the detector 6. The obtained data is stored in a memory 13, together with information about addresses.

The stored data is processed by the CPU 11 in the manner described below. The stored data is divided into blocks according to the individual reaction cells. The positions, or addresses, at which the amount of light is minimal, are recognized as the edges of the container of each reaction cell. In this way, the addresses AX and AY of two edges X and Y of one reaction cell are found. Then, the address of the midpoint between the addresses of these two edges X and Y is found, using a formula (AX+AY)/2. This midpoint is taken as a center. If data is taken from 50 sampling points located ahead of the center, from the center, and from 50 sampling points located behind the center, then the address of the measurement starting point for this reaction cell is given by

{(AX+AY)/2}−50.

The maximum number of accepted sampling points is equal to the number of points of the measurable interval, or 102. If the number of the accepted sampling points is too large, photometric data will be taken from vicinities of the inner wall of the reaction cell with unfavorable results. In practice, using only values taken from vicinities of the center of the cell is advantageous for the measuring accuracy. Therefore, it is desired to select 40 sampling points ahead of the center point, a sampling point at the center, and 40 sampling points behind the center point. Thus, 81 sampling points are selected. Alternatively, 30 sampling points ahead of the center point, a sampling point at the center, and 30 sampling points behind the center point may be selected. In total, 61 sampling points are selected.

As a modified embodiment, the address AX of only one edge X is found. The number of points 77 from the aforementioned edge of the reaction cell to the measurable position (measurement starting point) is added to the address AX. The sum (AX+77) is taken as the address of the measurement starting point.

If variations in shape and size among the reaction cells are sufficiently small, and if they are mounted to the turntable with sufficiently high accuracy and equally spaced from each other circumferentially on the turntable, then the address A001 of the measurement starting position for one reaction cell C1 is determined as described above. Addresses of measurement starting positions for subsequent reaction cells are respectively given by A001+556, A001+556+556, and so forth. In this way, the number of encoder pulses 556 corresponding to the pitch between the successive cells is sequentially added. The data obtained by calculations in this way is stored in the setting register.

Figure 4:
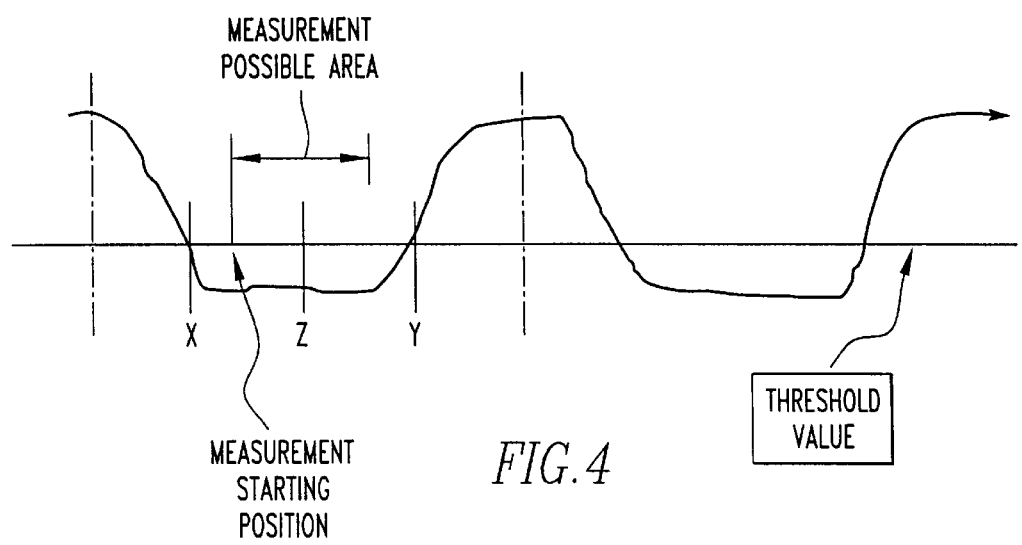
FIG. 4 is a diagram illustrating another method of finding a position at which measurement of a reaction cell is started.

FIG. 4 illustrates another method of determining measurement starting points. In this example, a liquid solution exhibiting absorbance is metered into reaction cells. Then, measurements are made to determine the measurement starting positions. If data is obtained by measurements as illustrated in FIG. 4, a threshold value corresponding to some absorbance is set. The intersections of a straight line indicating this threshold value and a curve obtained by plotting data derived by measurements are found. The addresses of the intersections are taken as encoder addresses at the edges X and Y of each reaction cell. In the same way as in FIG. 3, the address of a measurement starting point for each reaction cell is found from the addresses of the edges X and Y.

Where the turntable is driven by a motor equipped with no encoder, it is obvious that the encoder needs to be connected to the driving shaft of the turntable.

As described thus far, in accordance with the present invention, the timing at which a measurement for each reaction cell is started is determined precisely with the encoder. Therefore, accurate measurements determined by the resolution of the encoder can be performed with high reproducibility. Furthermore, it is not necessary that the turntable be provided with slits used for starting of measurements corresponding to reaction cells. Consequently, the cost of the automatic chemical analyzer can be curtailed.

Having thus described our invention with the detail and particularity required by the Patent Laws, what is desired protected by Letters Patent is set forth in the following claims.

What is claimed is:

1. A measuring system for use with an automatic chemical analyzer, said measuring system comprising:

a turntable on which plural reaction cells are arranged circumferentially, each of said reaction cells holding a sample to be measured;

a detector located in a fixed position relative to said turntable and acting to measure absorbances of said reaction cells in turn as said turntable rotates;

a direct drive motor having an encoder, the direct drive motor connected to said turntable and the encoder producing an output signal comprising a plurality of pulses as the turntable rotates between the center points of each reaction cell, said pulses generated each time said turntable rotates through a given angle;

a counter for creating an address signal from the output signal from said encoder;

a comparator for comparing said address signal produced from said counter with address values previously found when said reaction cells arrive at a detection position, said comparator producing a coincidence signal when a match is found; and means for starting acceptance of absorbance measurements from said detector corresponding to said reaction cells in response to the coincidence signal from said comparator.

2. The measuring system of claim 1, wherein there is further provided a position sensor for producing an output signal when a certain position on said turntable arrives at a given position relative to said detector, and wherein said counter is reset to an initial value in response to said output signal from said position sensor.

3. The measuring system of claim 2, further comprising an AND circuit, wherein the output signal from said position sensor and the output signal from said encoder are ANDed to produce an AND circuit output, and wherein said counter is reset to an initial value in response to said AND circuit output.

4. The measuring system of any one of claims 1 to 3, further comprising: a register for storing previously found address values of said reaction cells when each arrives at the detection position; and a readout means for sequentially reading address values for reaction cells to be measured subsequently from said register in response to said coincidence signal and sending the address values to said comparator.

5. A measuring system for use with an automatic chemical analyzer, said measuring system comprising:

a turntable on which plural reaction cells are arranged circumferentially, each of said reaction cells holding a sample to be measured;

a detector located in a fixed position relative to said turntable and acting to measure absorbances of said reaction cells in turn as said turntable rotates;

a direct drive motor having an encoder, the direct drive motor connected to said turntable and the encoder producing an output signal comprising a plurality of pulses as the turntable rotates between the center points of each reaction cell, said pulses generated each time said turntable rotates through a given angle;

a counter for creating an address signal from the output signal from said encoder;

a CPU means for initially determining address values when said reaction cells each arrive at a detection position by sampling the output signal from said detector in synchronism with the output signal from said encoder when no liquid solution is put in said reaction cells or a liquid exhibiting no absorbance in the measured photometric range is put in said reaction cells and identifying positions at which the amount of detected absorbance is indicative of edge points of each of said reaction cells;

a comparator for comparing said address signal produced from said counter with address values previously found when said reaction cells arrive at a detection position, said comparator producing a coincidence signal when a match is found; and means for starting acceptance of absorbance measurements from said detector corresponding to said reaction cells in response to the coincidence signal from said comparator.

6. A measuring system for use with an automatic chemical analyzer, said measuring system comprising:

a turntable on which plural reaction cells are arranged circumferentially, each of said reaction cells holding a sample to be measured;

a detector located in a fixed position relative to said turntable and acting to measure absorbances of said reaction cells in turn as said turntable rotates;

a direct drive motor having an encoder, the direct drive motor connected to said turntable and the encoder producing an output signal comprising a plurality of pulses as the turntable rotates between the center points of each reaction cell, said pulses generated each time said turntable rotates through a given angle;

a counter for creating an address signal from the output signal from the said encoder;

a CPU means for initially determining address values when said reaction cells each arrive at and depart from a detection position by sampling the output signal from said detector in synchronism with said output signal of said encoder when no liquid solution is put in said reaction cells or a liquid exhibiting no absorbance in the photometric range is put in said reaction cells by finding positions at which the light is minimal or no longer minimal and treating said positions as edge points of each of said reaction cells;

a comparator for comparing said address signal produced from said counter with address values previously found when said reaction cells arrive at a detection position, said comparator producing a coincidence signal when a match is found; and means for starting acceptance of absorbance measurements from said detector corresponding to said reaction cells in response to the coincidence signal from said comparator.

7. A measuring system for use with an automatic chemical analyzer, said measuring system comprising:

a turntable on which plural reaction cells are arranged ciicumferentially, each of said reaction cells holding a sample to be measured;

a detector located in a fixed position relative to said turntable and acting to measure absorbances of said reaction cells in turn as said turntable rotates;

a direct drive motor having an encoder, the direct drive motor connected to said turntable and the encoder producing an output signal comprising a plurality of pulses as the turntable rotates between the center points of each reaction cell, said pulses generated each time said turntable rotates through a given angle;

a counter for creating an address signal from the output signal from said encoder;

a CPU means for initially determining address values when said reaction cells each arrive at a detection position by sampling the output signal from said detector in synchronism with the output signal from said encoder when a liquid exhibiting absorbance in a measured spectral range is put in said reaction cells and identifying positions at which the amount of detected absorbance is indicative of edge points of said reaction cells;

a comparator for comparing said address signal produced from said counter with address values previously found when said reaction cells arrive at a detection position, said comparator producing a coincidence signal when a match is found; and means for starting acceptance of absorbance measurements from said detector corresponding to said reaction cells in response to the coincidence signal from said comparator.

8. A measuring system for use with an automatic chemical analyzer, said measuring system comprising:

a turntable on which plural reaction cells are arranged circumferentially, each of said reaction cells holding a sample to be measured;

a detector located in a fixed position relative to said turntable and acting to measure absorbances of said reaction cells in turn as said turntable rotates;

a direct drive motor having an encoder, the direct drive motor connected to said turntable and the encoder producing an output signal comprising a plurality of pulses as the turntable rotates between the center points of each reaction cell, said pulses generated each time said turntable rotates through a given angle;

a counter for creating an address signal from the output signal from said encoder;

a CPU means for initially determining address values when said reaction cells each arrive at and depart from a detection position by sampling the output signal from said detector in synchronism with the output signal from said encoder when a liquid exhibiting absorbance in a measured spectral range is put in said reaction by finding positions at which the absorbance assumes a given value or no longer assumes a given value and treating these positions as the edge points of each of said reaction cells;

a comparator for comparing said address signal produced from said counter with address values previously found when said reaction cells arrive at a detection position, said comparator producing a coincidence signal when a match is found; and means for starting acceptance of absorbance measurements from said detector corresponding to said reaction cells in response to the coincidence signal from said comparator.

* * * * *